(12) United States Patent
Ayyadurai et al.

(10) Patent No.: US 12,167,997 B2
(45) Date of Patent: Dec. 17, 2024

(54) ANTI-OXIDANT COMPOSITIONS

(71) Applicant: CytoSolve, Inc., Cambridge, MA (US)

(72) Inventors: V. A. Shiva Ayyadurai, Cambridge, MA (US); Prabhakar Deonikar, Cambridge, MA (US)

(73) Assignee: CytoSolve, Inc., Cambridge, MA (US)

( * ) Notice: Subject to any disclaimer, the term of this patent is extended or adjusted under 35 U.S.C. 154(b) by 0 days.

(21) Appl. No.: 18/185,711

(22) Filed: Mar. 17, 2023

(65) Prior Publication Data

US 2023/0293486 A1     Sep. 21, 2023

Related U.S. Application Data (60) Provisional application No. 63/321,522, filed on Mar. 18, 2022.

(51) Int. Cl.
| | |
|---|---|
| *A61K 31/375* | (2006.01) |
| *A61K 31/07* | (2006.01) |
| *A61K 31/353* | (2006.01) |
| *A61K 31/355* | (2006.01) |
| *A61P 39/06* | (2006.01) |

(52) U.S. Cl.
CPC ............ *A61K 31/375* (2013.01); *A61K 31/07* (2013.01); *A61K 31/353* (2013.01); *A61K 31/355* (2013.01); *A61P 39/06* (2018.01)

(58) Field of Classification Search
CPC .... A61K 31/375; A61K 31/07; A61K 31/353; A61K 31/355; A61P 39/06
See application file for complete search history.

(56) References Cited

U.S. PATENT DOCUMENTS

2006/0099239 A1 *    5/2006   Coleman ............... A23L 33/175
                                                                                                                          514/561

FOREIGN PATENT DOCUMENTS

CN            103300364 A   *    9/2013
WO     WO-2015003246 A1  *   1/2015  ........... A61K 31/341

* cited by examiner

*Primary Examiner* — Medhanit W Bahta
*Assistant Examiner* — Manahil Mirghani Ali Abdalhameed
(74) *Attorney, Agent, or Firm* — Oblon, McClelland, Maier & Neustadt, L.L.P.

(57) ABSTRACT

The present disclosure is related to dietary supplements. For example, this disclosure relates to compositions that include, one or more agents that decrease the production of reactive oxygen species (ROS) responsible for oxidative stress, and/or decrease the concentration of ROS. In some embodiments, a composition as provided herein includes epicatechin present in an amount of about 0.1% to about 3% w/w of the composition; vitamin A acid present in an amount of about 1% to about 15% w/w of the composition; vitamin C present in an amount of about 10% to about 80% w/w of the composition; and, vitamin E present in an amount of about 5% to about 60% w/w of the composition. Such compositions are useful for improving oxidative stress by decreasing ROS concentration.

5 Claims, 5 Drawing Sheets

Figure 1

ANTI-OXIDANT COMPOSITIONS

This application claims benefit of provisional application 63/321,522 the entire contents of which is incorporated herein by reference.

TECHNICAL FIELD

This disclosure is related to the field of dietary supplements. For example, this disclosure relates to compositions useful for anti-oxidant effects. Such compositions can include, for example, one or more agents that lower the concentration reactive oxygen species.

BACKGROUND

Oxidative stress is a physiological phenomenon that plays an important role in health and disease. Reactive oxygen species (ROS) are produced as a by-product of oxygen metabolism and are cleared by the anti-oxidant enzymes system under normal health conditions. Any imbalance between production and accumulation of ROS and their clearance by the anti-oxidant enzymes system leads to a phenomenon known as oxidative stress. At low or moderate concentrations, ROS can be beneficial in boosting the host defense system by fighting pathogens; however, excess production of ROS can lead to several chronic and acute pathologies such as cancer, cardiovascular disease, neurological disease, respiratory disease, rheumatoid arthritis, osteoarthritis, renal dysfunction, and sexual dysfunction.

Superoxide radicals ($O_2^{*-}$), hydrogen peroxide ($H_2O_2$), hydroxyl radicals ($\cdot OH$), and singlet oxygen ($^1O_2$) are some of the common ROS. They are generated as metabolic by-products by biological systems. Processes, like protein phosphorylation, activation of several transcriptional factors, apoptosis, immunity, and differentiation, are all dependent on a proper ROS production and presence inside cells that need to be kept at a low level. ROS are mainly produced by mitochondria, during both physiological and pathological conditions, that is, $O_2^{*-}$ can be formed by cellular respiration, by lipoxygenases (LOX) and cyclooxygenases (COX) during the arachidonic acid metabolism, and by endothelial and inflammatory cells.

The effects of ROS generated by oxidative stress are counteracted by enzymatic and non-enzymatic modes in the body. Enzymes such as superoxide dismutase, catalase, and glutathione peroxidase are involved in mitigation of oxidative stress. The body also produces anti-oxidant molecules such as lipolic acid, glutathione, L-arginine, and coenzyme Q10 that neutralize the ROS. In addition to these enzymes and molecules, there are several exogenous antioxidant molecules of animal or vegetal origin, mainly introduced by diet or by nutritional supplementation. Methods and compositions that include the exogenous antioxidant molecules for lowering oxidative stress are highly desirable.

SUMMARY

Provided herein are methods for improving oxidative stress in a subject in need thereof comprising administering to the subject a composition comprising two or more agents that decrease ROS concentrations.

In some embodiments, oxidative stress is associated with one or more of: cellular toxicity, infection, cancer, cardiovascular diseases such as atherosclerosis, neurodegenerative diseases such as Parkinson's disease, Alzheimer's disease, amyotrophic lateral sclerosis (ALS), multiple sclerosis, depression, and memory loss, obesity, stress, diabetes mellitus, or aging.

In some embodiments, at least one agent that lowers the concentration of ROS also decreases production of ROS; or a combination thereof.

In some embodiments, at least one agent that decreases the concentration of ROS.

In some embodiments, at least one agent that decreases the concentration of ROS modulates oxidative stress pathway.

In some embodiments, the two or more agents that decrease concentration of ROS comprise one or more of: a flavan; a retinoic acid; a carboxylic acid; and, a benzopyran.

Also provided herein are methods for improving oxidative stress in a subject in need thereof comprising administering to the subject a composition comprising two or more agents that decrease the concentration of ROS, decrease the production of ROS; or a combination thereof.

In some embodiments, oxidative stress is associated with one or more of: cellular toxicity, infection, cancer, cardiovascular diseases such as atherosclerosis, neurodegenerative diseases such as Parkinson's disease, Alzheimer's disease, amyotrophic lateral sclerosis (ALS), multiple sclerosis, depression, and memory loss, obesity, stress, diabetes mellitus, or aging.

In some of any of the above embodiments, the flavan is flavan 3-ols. In some embodiments, the flavan 3-ols is selected from the group consisting of: epicatechin, procyanidin C1, procyanidin B2, cinnamtannin A2, and a combination thereof.

In some embodiments, the flavan is epicatechin.

In some embodiments, the flavan is present in an amount of about 0.05% to about 5% w/w of the composition. In some embodiments, the flavan is present in an amount of about 0.1% to about 3% w/w of the composition. In some embodiments, the flavan is present in an amount of about 0.25% to about 1% w/w of the composition. In some embodiments, the flavan is present in an amount of about 0.75% w/w of the composition.

In some of any of the above embodiments, the retinoic acid is an all-trans-retinol. In some embodiments, the retinoic acid is selected from the group consisting of: vitamin A, 13,14-dihydroretinoic acid, and a combination thereof.

In some embodiments, the retinoic acid is vitamin A.

In some embodiments, the retinoic acid is present in an amount of about 0.5% to about 20% w/w of the composition. In some embodiments, the retinoic acid is present in an amount of about 1% to about 15% w/w of the composition. In some embodiments, the retinoic acid is present in an amount of about 2% to about 10% w/w of the composition. In some embodiments, the retinoic acid is present in an amount of about 4.5% w/w of the composition.

In some of any of the above embodiments, the carboxylic acid is a ketoaldonic acid. In some embodiments, the carboxylic acid is selected from the group consisting of: D- or L-ascorbic acid (vitamin C), erythorbic acid, gulonic acid, and a combination thereof.

In some embodiments, the carboxylic acid is vitamin C.

In some embodiments, the carboxylic acid is present in an amount of about 1% to about 99% w/w of the composition. In some embodiments, the carboxylic acid is present in an amount of about 10% to about 80% w/w of the composition. In some embodiments, the carboxylic acid is present in an amount of about 40% to about 77% w/w of the composition. In some embodiments, the carboxylic acid is present in an amount of about 66% w/w of the composition.

In some embodiments, the benzopyran is a chromanol. In some embodiments, the benzopyran is selected from the group consisting of: α-tocopherol, β-tocopherol, γ-tocopherol, δ-tocopherol, α-tocotrienol, β-tocotrienol, γ-tocotrienol, δ-tocotrienol, and a combination thereof.

In some embodiments, benzopyran is a combination of α-tocopherol, β-tocopherol, γ-tocopherol, and δ-tocopherol (vitamin E).

In some embodiments, the benzopyran is present in an amount of about 1% to about 90% w/w of the composition. In some embodiments, the benzopyran is present in an amount of about 5% to about 60% w/w of the composition. In some embodiments, the benzopyran is present in an amount of about 15% to about 40% w/w of the composition. In some embodiments, the benzopyran is present in an amount of about 28.75% w/w of the composition.

In some embodiments, the flavan is epicatechin; the retinoic acid is vitamin A; the carboxylic acid is vitamin C; and, the benzopyran is vitamin E.

In some embodiments, the composition comprises two or more of: epicatechin; vitamin A; vitamin C; and, vitamin E. In some embodiments, the composition comprises three or more of: epicatechin; vitamin A; vitamin C; and, vitamin E.

In some embodiments, the composition comprises: epicatechin is present in an amount of about 0.25% to about 1% w/w of the composition; vitamin A present in an amount of about 2% to about 10% w/w of the composition; vitamin C present in an amount of about 40% to about 77% w/w of the composition; and, vitamin E present in an amount of about 15% to about 40% w/w of the composition.

In some embodiments, the composition comprises: epicatechin present in an amount of about 0.75% w/w of the composition; vitamin A is present in an amount of about 4.5% w/w of the composition; vitamin C is present in an amount of about 66% w/w of the composition; and, vitamin E is present in an amount of about 28.75% w/w of the composition.

In some embodiments, the composition further comprises one or more excipients, diluents, or carriers.

In some embodiments, the composition is administered orally.

In some embodiments, the composition is a configured as a powder.

Also provided herein is a method for decreasing ROS concentration of a subject comprising administering to the subject a composition as described herein.

The details of one or more embodiments of the invention are set forth in the accompanying drawings and the description below. Other features, objects, and advantages of the invention will be apparent from the description and drawings, and from the claims.

DETAILED DESCRIPTION

Oxidative stress is a phenomenon caused by an imbalance between production and accumulation of oxygen reactive species (ROS) in cells and tissues and the ability of a biological system to detoxify these reactive products. Superoxide radicals ($O_2^{*-}$), hydrogen peroxide ($H_2O_2$), hydroxyl radicals (·OH), and singlet oxygen ($^1O_2$) are commonly defined reactive oxygen species (ROS), they are generated as metabolic by-products by biological systems. Processes, like protein phosphorylation, activation of several transcriptional factors, apoptosis, immunity, and differentiation, are all dependent on a proper ROS production and presence inside cells that need to be kept at a low level. When ROS production increases, they start showing harmful effects on important cellular structures like proteins, lipids, and nucleic acids. A large body of evidences shows that oxidative stress can be responsible, with different degrees of importance, in the onset and/or progression of several diseases (i.e., cancer, diabetes, metabolic disorders, atherosclerosis, and cardiovascular diseases).

Body's defenses to excessive oxidative stress include modulation via enzymatic and non-enzymatic methods. Antioxidant enzymes such as SOD, catalase, glutathione peroxidase maintain the oxidative stress by converting ROS to harmless end-products such as water, where as non-enzymatic antioxidant molecules such as lipoic acid, glutathione, L-arginine, and coenzyme Q10, neutralize ROS directly. However, these defenses against oxidative stress may not be sufficient in under chronic oxidative conditions that lead to several cardiovascular, neurological, and metabolic disorders. Compositions, as described herein, mitigate oxidative stress via decreasing the ROS levels and lowering ROS production.

Accordingly, the present disclosure provides methods and compositions (e.g., dietary supplements) related to decrease oxidative stress. Such compositions can contain two or more agents that reduce the concentrations of ROS, decrease the production of ROS, or a combination thereof, useful for improvement in reduction in oxidative stress.

DEFINITIONS

As used herein, the phrase "oxidative stress" or "low concentrations of ROS" a disease, disorder, or condition encompasses a subject with high concentrations of ROS that has also been diagnosed with, was previously diagnosed with, or has symptoms associated with the disease, disorder, or condition.

As used herein, the phrases an "effective amount" or a "therapeutically effective amount" of an active agent or ingredient, or pharmaceutically active agent or ingredient, refer to an amount of the active agent sufficient enough to reduce or eliminate one or more symptoms of the disorder or to effect a cure upon administration. Effective amounts of the active agent will vary with the kind of active agent chosen, the particular condition or conditions being treated, the severity of the condition, the duration of the treatment, the specific components of the composition being used, and like factors.

As used herein, "subject" refers to any subject, particularly a mammalian subject, for whom diagnosis, prognosis, or therapy is desired, for example, a human.

Reference to the term "about" has its usual meaning in the context of compositions to allow for reasonable variations in amounts that can achieve the same effect and also refers herein to a value of plus or minus 10% of the provided value. For example, "about 20" means or includes amounts from 18 to and including 22.

As used herein, a "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. A useful composition herein needs only to reduce the severity of a disease, disorder, or condition, reduce the severity of one or more symptoms associated therewith, or provide improvement to a patient or subject's quality of life.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. As used herein, the singular form "a", "an", and "the" include plural references unless indicated otherwise. For example, "an" excipient includes one or more excipients. It is understood that aspects and variations of the invention described herein include "consisting of" and/or "consisting essentially of" aspects and variations. Methods and materials are described herein for use in the present invention; other, suitable methods and materials known in the art can also be used. The materials, methods, and examples are illustrative only and not intended to be limiting. All publications, patent applications, patents, sequences, databases entries, and other references mentioned herein are incorporated by reference in their entirety.

Agents that Decrease Oxidative Stress

In some embodiments, a composition as described herein can comprise an agent that decreases oxidative stress. For example, in some embodiments, an agent that decreases oxidative stress is an agent that decrease the concentration of ROS. As another example, an agent that decreases oxidative stress can be an agent that decreases production of ROS. Many agents that decrease the concentration of ROS are known to one of skill in the art. Non-limiting examples of an agent that decreases the concentration of ROS include epicatechin, vitamin A, vitamin C, and vitamin E. Several methods for measuring ROS are known to one of ordinary skill in the art. Non-limiting examples of such methods include: measuring ROS concentration using fluorescence spectroscopy (see, for example, Pavelescu, L. A. *J. Med. Life.* 2015, 8 (Spec Issue): 38-42; Woolley et al. *Trends Biochem. Sci.* 2013. November; 38(11):556-65.; and Yannick et al. *Oxid Med Cell Longev.* 2012 April; 2013, Article ID 862423, 15 pages; each of which are incorporated by reference herein in their entireties).

In some embodiments, an agent that decrease the concentration of ROS by at least 0.5%, 1%, 5%, 10%, or 15%. For example, the agent that decreases the production of ROS decreases the concentration of ROS by about 1%, about 2%, about 3%, about 4%, about 5%, about 10%, about 15% or more.

Flavans

In some embodiments, a composition as described herein includes a flavan that modulates oxidative stress. In some embodiments, a composition as described herein includes a flavan that reduces ROS production. In some embodiments, a composition as described herein includes a flavan that decreases ROS concentrations.

As described herein, a "flavan" refers to a molecule derived from benzopyran that use the 2-phenyl-3,4-dihydro-2H-chromene skeleton.

Non-limiting examples of flavans include flavan-3-ols, flavan-4-ols and flavan-3,4-diols. Examples of a flavan-3-ols include, without limitation, epicatechin, catechin, epigallocatechin, fisetinidol, EGCG. Non-limiting examples of flavans that decreases oxidative stress concentration include epicatechin.

Retinoic Acids

In some embodiments, a composition as described herein includes a retinoic acid that modulates oxidative stress. In some embodiments, a composition as described herein includes a retinoic acid that decreases the ROS production. In some embodiments, a composition as described herein includes a retinoic acid that decreases ROS concentrations.

As described herein a "retinoic acid" refers to a compound containing all four exocyclic double bonds with E-(trans-) geometry.

Non-limiting examples of a retinoic acid include all-trans-retinol. Examples of all-trans-retinol include vitamin A and 13, 14-dihydroretinoic acid. Non-limiting examples of retinoic acids that can reduce ROS concentration include vitamin A.

Carboxylic Acids

In some embodiments, a composition as described herein includes a carboxylic acid that modulates oxidative stress. In some embodiments, a composition as described herein includes a carboxylic acid that decreases the ROS production. In some embodiments, a composition as described herein includes a carboxylic acid that reduce ROS concentrations.

As described herein a "carboxylic acid" refers to a compound containing a —COOH.

Non-limiting examples of a carboxylic acid include ketoaldonic acid. Examples of ketoaldonic acid include, without limitation, D- or L-ascorbic acid (vitamin C), erythorbic acid, and gulonic acid. Non-limiting examples of carboxylic acids that can reduce ROS concentration include vitamin C.

Benzopyrans

In some embodiments, a composition as described herein includes a benzopyran that modulates oxidative stress. In some embodiments, a composition as described herein includes a benzopyran that decreases the ROS concentrations. In some embodiments, a composition as described herein includes a benzopyran that decreases ROS production.

As described herein, a "benzopyran" refers to a polycyclic organic compound comprising a benzene ring fused to a pyran ring.

Non-limiting examples of benzopyran include chromonols. Examples of a chromonols include, without limitation, α-tocopherol, β-tocopherol, γ-tocopherol, and δ-tocopherol (vitamin E). Non-limiting examples of benzopyran that can decrease oxidative stress include α-tocopherol, β-tocopherol, γ-tocopherol, and δ-tocopherol (vitamin E).

Dietary Supplemental Compositions

The present disclosure provides compositions (e.g., dietary supplements) containing two or more agents that decrease the production of ROS, decrease the concentration of ROS, or a combination thereof. For example, in some embodiments, the present disclosure provides a compositions comprising two or more agents that decrease the production of ROS. As another example, in some embodiments, the present disclosure provides a composition comprising two or more agents that decrease the production of ROS, decrease the concentration of ROS; or a combination thereof. In some embodiments, the present disclosure provides compositions comprising a flavan, a retinoic acid, a carboxylic acid, and a benzopyran. Such compositions can be used to decrease oxidative stress. In addition, the disclosure provides methods for relieving symptoms caused by oxidative stress associated with one or more of: cellular toxicity, infection, cancer, cardiovascular diseases such as atherosclerosis, neurodegenerative diseases such as Parkinson's disease, Alzheimer's disease, amyotrophic lateral sclerosis (ALS), multiple sclerosis, depression, and memory loss, obesity, stress, diabetes mellitus, or aging. Such methods involve the administration of a composition as provided herein.

In some embodiments, a composition as described herein includes two or more agents that decrease ROS concentrations. In some embodiments, at least one of the agents that decrease ROS concentrations also decreases ROS production. In some embodiments, the two or more agents that decrease oxidative stress include a flavan, a retinoic acid, a carboxylic acid, and a benzopyran.

In some embodiments, a composition as described herein includes a flavan that can modulate oxidative stress. In some embodiments, a composition as described herein includes a flavan that decreases ROS concentration. In some embodiments, a composition as described herein includes a flavan that decreases ROS production.

As described herein, a "flavan" refers to a molecule derived from benzopyran that use the 2-phenyl-3,4-dihydro-2H-chromene skeleton. Non-limiting examples of flavans include flavan-3-ols, flavan-4-ols and flavan-3,4-diols. Examples of a flavan-3-ols include, without limitation, epicatechin, catechin, epigallocatechin, fisetinidol, EGCG. Non-limiting examples of flavans that can decrease ROS concentration include epicatechin.

In some embodiments, a flavan is present in an amount of about 0.025% to about 2% w/w of the composition. For example, about 0.025% to about 0.2%, about 0.025% to about 0.4%, about 0.025% to about 0.6%, about 0.025% to about 0.8%, about 0.025% to about 1%, about 0.025% to about 1.2%, about 0.025% to about 1.4%, about 0.025% to about 1.6%, about 0.025% to about 1.8%, about 0.025% to about 1.9%, about 1.9% to about 2%, about 1.8% to about 2%, about 1.6% to about 2%, about 1.4% to about 2%, about 1.2% to about 2%, about 1% to about 2%, about 0.8% to about 2%, about 0.6% to about 2%, about 0.4% to about 2%, about 0.2% to about 2%, about 0.1% to about 2%, or about 0.05% to about 1% w/w of the composition. In some embodiments, a flavan is present in an amount of about 0.025% to about 1% w/w of the composition. For example, about 0.025% to about 0.075, about 0.025% to about 0.125%, about 0.025% to about 0.175%, about 0.025% to about 0.225%, about 0.025% to about 0.275%, about 0.025% to about 0.325%, about 0.025% to about 0.375%, about 0.025% to about 0.425%, about 0.025% to about 0.475%, about 0.025% to about 0.525%, about 0.025% to about 0.575%, about 0.025% to about 0.625%, about 0.025% to about 0.675%, about 0.025% to about 0.725%, about 0.025% to about 0.775%, about 0.025% to about 0.825%, about 0.025% to about 0.875%, about 0.025% to about 0.925%, about 0.025% to about 0.975%, about 0.975% to about 1%, about 0.925% to about 1%, about 0.875% to about 1%, about 0.825% to about 1%, about 0.775% to about 1%, about 0.725% to about 1%, about 0.675% to about 1%, about 0.625% to about 1%, about 0.575% to about 1%, about 0.525% to about 1%, about 0.475% to about 1%, about 0.425% to about 1%, about 0.375% to about 1%, about 0.325% to about 1%, about 0.275% to about 1%, about 0.225% to about 1%, about 0.175% to about 1%, about 0.125% to about 1%, about 0.075% to about 1%, or about 0.05% to about 1% w/w of the composition. In some embodiments, a flavan is present in an amount of about 0.025%, about 0.05%, about 0.075%, about 0.1%, about 0.125%, about 0.15%, about 0.175%, about 0.2%, about 0.225%, about 0.25%, about 0.275%, about 0.3, about 0.325%, about 0.35%, about 0.375%, about 0.4%, about 0.425%, about 0.45%, about 0.475%, about 0.5%, about 0.525%, about 0.55%, about 0.575%, about 0.6%, about 0.625%, about 0.65%, about 0.65%, about 0.675%, about 0.7%, about 0.725%, about 0.75%, about 0.775%, about 0.8%, about 0.825%, about 0.85%, about 0.875%, about 0.9%, about 0.925%, about 0.95%, about 0.975%, or about 1% w/w of the composition.

In some embodiments, the flavan is a flavan 3-ols. In some embodiments, the flavan 3-ol is selected from the group consisting of: epicatechin, catechin, epigallocatechin, fisetinidol, EGCG, and a combination thereof.

In some embodiments, the flavan is epicatechin. In some embodiments, epicatechin is present in an amount of about 0.025% to about 2% w/w of the composition. For example, about 0.025% to about 0.2%, about 0.025% to about 0.4%, about 0.025% to about 0.6%, about 0.025% to about 0.8%, about 0.025% to about 1%, about 0.025% to about 1.2%, about 0.025% to about 1.4%, about 0.025% to about 1.6%, about 0.025% to about 1.8%, about 0.025% to about 1.9%, about 1.9% to about 2%, about 1.8% to about 2%, about 1.6% to about 2%, about 1.4% to about 2%, about 1.2% to about 2%, about 1% to about 2%, about 0.8% to about 2%, about 0.6% to about 2%, about 0.4% to about 2%, about 0.2% to about 2%, about 0.1% to about 2%, or about 0.05% to about 1% w/w of the composition. In some embodiments, epicatechin is present in an amount of about 0.025% to about 1% w/w of the composition. For example, about 0.025% to about 0.075, about 0.025% to about 0.125%, about 0.025% to about 0.175%, about 0.025% to about 0.225%, about 0.025% to about 0.275%, about 0.025% to about 0.325%, about 0.025% to about 0.375%, about 0.025% to about 0.425%, about 0.025% to about 0.475%, about 0.025% to about 0.525%, about 0.025% to about 0.575%, about 0.025% to about 0.625%, about 0.025% to about 0.675%, about 0.025% to about 0.725%, about 0.025% to about 0.775%, about 0.025% to about 0.825%, about 0.025% to about 0.875%, about 0.025% to about 0.925%, about 0.025% to about 0.975%, about 0.975% to about 1%, about 0.925% to about 1%, about 0.875% to about 1%, about 0.825% to about 1%, about 0.775% to about 1%, about 0.725% to about 1%, about 0.675% to about 1%, about 0.625% to about 1%, about 0.575% to about 1%, about 0.525% to about 1%, about 0.475% to about 1%, about 0.425% to about 1%, about 0.375% to about 1%, about 0.325% to about 1%, about 0.275% to about 1%, about 0.225% to about 1%, about 0.175% to about 1%, about 0.125% to about 1%, about 0.075% to about 1%, or about 0.05% to about 1% w/w of the composition. In some embodiments, epicatechin is present in an amount of about 0.025%, about 0.05%, about 0.075%, about 0.1%, about 0.125%, about 0.15%, about 0.175%, about 0.2%, about 0.225%, about 0.25%, about 0.275%, about 0.3, about 0.325%, about 0.35%, about 0.375%, about 0.4%, about 0.425%, about 0.45%, about 0.475%, about 0.5%, about 0.525%, about 0.55%, about 0.575%, about 0.6%, about 0.625%, about 0.65%, about 0.65%, about 0.675%, about 0.7%, about 0.725%, about 0.75%, about 0.775%, about 0.8%, about 0.825%, about 0.85%, about 0.875%, about 0.9%, about 0.925%, about 0.95%, about 0.975%, or about 1% w/w of the composition.

In some embodiments, a composition as described herein includes a retinoic acid that can modulate oxidative stress. In some embodiments, a composition as described herein includes a retinoic acid that decreases ROS concentration.

As described herein a "retinoic acid" refers to a compound containing all four exocyclic double bonds with E-(trans-) geometry. Non-limiting examples of a retinoic acid include all-trans-retinol. Examples of all-trans-retinol include vitamin A and 13, 14-dihydroretinoic acid. Non-limiting examples of retinoic acids that can reduce ROS concentration include vitamin A.

In some embodiments, a retinoic acid is present in an amount of about 0.5% to about 20% w/w of the composition. For example, about 0.5% to about 1%, about 0.5% to about 5%, about 0.5% to about 10%, about 0.5% to about 15%, about 0.5% to about 20%, about 15% to about 20%, about 10% to about 20%, about 5% to about 20%, or about 1% to about 20% w/w of the composition. In some embodiments, a retinoic acid is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, a retinoic acid is present in an amount of about 2%, about 2.2%, about 2.4%, about 2.6%, about 2.8%, about 3%, about 3.2%, about 3.4%, about 3.6%, about 3.8%, about 4%, about 4.2%, about 4.4%, about 4.6%, about 4.8%, about 5%, about 5.2%, about 5.4%, about 5.6%, about 5.8%, about 6%, about 6.2%, about 6.4%, about 6.6%, about 6.8%, about 7%, about 7.2%, about 7.4%, about 7.6%, about 7.8%, about 8%, about 8.2%, about 8.4%, about 8.6%, about 8.8%, about 9%, about 9.2%, about 9.4%, about 9.6%, about 9.8%, or about 10% w/w of the composition.

In some embodiments, the retinoic acid is a all-trans-retinol. In some embodiments, the retinoic acid is selected from the group consisting of: vitamin A and 13, 14-dihydroretinoic acid, and a combination thereof.

In some embodiments, the retinoic acid is vitamin A. In some embodiments, vitamin A is present in an amount of about 0.5% to about 20% w/w of the composition. For example, about 0.5% to about 1%, about 0.5% to about 5%, about 0.5% to about 10%, about 0.5% to about 15%, about 0.5% to about 20%, about 15% to about 20%, about 10% to about 20%, about 5% to about 20%, or about 1% to about 20% w/w of the composition. In some embodiments, vitamin A is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, vitamin A is present in an amount of about 2%, about 2.2%, about 2.4%, about 2.6%, about 2.8%, about 3%, about 3.2%, about 3.4%, about 3.6%, about 3.8%, about 4%, about 4.2%, about 4.4%, about 4.6%, about 4.8%, about 5%, about 5.2%, about 5.4%, about 5.6%, about 5.8%, about 6%, about 6.2%, about 6.4%, about 6.6%, about 6.8%, about 7%, about 7.2%, about 7.4%, about 7.6%, about 7.8%, about 8%, about 8.2%, about 8.4%, about 8.6%, about 8.8%, about 9%, about 9.2%, about 9.4%, about 9.6%, about 9.8%, or about 10% w/w of the composition.

In some embodiments, a composition as described herein includes a carboxylic acid that can modulate oxidative stress. In some embodiments, a composition as described herein includes a carboxylic acid that decreases oxidative stress.

As described herein a "carboxylic acid" refers to a compound containing a —COOH. Non-limiting examples of a carboxylic acid include ketoaldonic acid. Examples of ketoaldonic acid include, without limitation, D- or L-ascorbic acid (vitamin C), erythorbic acid, and gulonic acid.

In some embodiments, a carboxylic acid is present in an amount of about 35% to about 95% w/w of the composition. For example, about 35% to about 45%, about 35% to about 55%, about 35% to about 65%, about 35% to about 75%, about 35% to about 85%, about 35% to about 90%, about 90% to about 95%, about 80% to about 95%, about 70% to about 95%, about 60% to about 95%, about 50% to about 95%, about 40% to about 95%, or about 30% to about 95% w/w of the composition. In some embodiments, a carboxylic acid is present in an amount of about 45% to about 75% w/w of the composition. For example, about 45% to about 50%, about 45% to about 55%, about 45% to about 60%, about 45% to about 65%, about 45% to about 70%, about 70% to about 75%, about 65% to about 75%, about 60% to about 75%, about 55% to about 75%, or about 50% to about 75% w/w of the composition. In some embodiments, a carboxylic acid is present in an amount of about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80% w/w of the composition.

In some embodiments, the carboxylic acid is a ketoaldonic acid. In some embodiments, the ketoaldonic acid is selected from the group consisting of: D- or L-ascorbic acid (vitamin C), erythorbic acid, gulonic acid, and a combination thereof.

In some embodiments, the carboxylic acid is ascorbic acid (vitamin C). In some embodiments, vitamin C is present in an amount of about 35% to about 95% w/w of the composition. For example, about 35% to about 45%, about 35% to about 55%, about 35% to about 65%, about 35% to about 75%, about 35% to about 85%, about 35% to about 90%, about 90% to about 95%, about 80% to about 95%, about 70% to about 95%, about 60% to about 95%, about 50% to about 95%, about 40% to about 95%, or about 30% to about 95% w/w of the composition. In some embodiments, vitamin C is present in an amount of about 45% to about 75% w/w of the composition. For example, about 45% to about 50%, about 45% to about 55%, about 45% to about 60%, about 45% to about 65%, about 45% to about 70%, about 70% to about 75%, about 65% to about 75%, about 60% to about 75%, about 55% to about 75%, or about 50% to about 75% w/w of the composition. In some embodiments, vitamin C is present in an amount of about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80% w/w of the composition.

In some embodiments, a composition as described herein includes a benzopyran that can modulate oxidative stress. In some embodiments, a composition as described herein includes a benzopyran that decreases ROS production. In some embodiments, a composition as described herein includes a benzopyran that decreases ROS concentrations.

As described herein, a "benzopyran" refers to a polycyclic organic compound comprising a benzene ring fused to a pyran ring. Non-limiting examples of benzopyran include chromonols. Examples of a chromonols include, without limitation, α-tocopherol, β-tocopherol, γ-tocopherol, and δ-tocopherol (vitamin E).

In some embodiments, a benzopyran is present in an amount of about 1% to about 70% w/w of the composition. For example, about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 1% to about 55%, about 1% to about 60%, about 1% to about 65%, about 65% to about 70%, 6 about 0% to about 70%, about 55% to about 70%, about 50% to about 70%, about 45% to about 70%, about 40% to about 70%, about 35% to about 70%, about 30% to about 70%, about 25% to about 70%, about 20% to about 70%, about 15% to about 70%, about 10% to about 70%, or about 5% to about 70% w/w of the composition. In some embodiments, a benzopyran is present in an amount of about 15% to about 35% w/w of the composition. For example, about 15% to about 17%, about 15% to about 19%, about 15% to about 21%, about 15% to about 23%, about 15% to about 25%, about 15% to about 27%, about 15% to about 29%, about 15% to about 31%, about 15% to about 33%, about 33% to about 35%, about 31% to about 35%, about 29% to about 35%, about 27% to about 35%, about 25% to about 35%, about 23% to about 35%, about 21% to about 35%, about 19% to about 35%, or about 17% to about 35% w/w of the composition. In some embodiments, a benzopyran is present in an amount of about 2%, about 15%, about 16%, about 17%, about 18%, about 19%, about 20%, about 21%, about 22%, about 23%, about 24%, about 25%, about 26%, about 27%, about 28%, about 28.15%, about 28.25%, about 28.35%, about 28.45%, about 28.55%, about 28.65%, about 28.75%, about 28.85%, about 28.95%, about 29%, about 30%, about 31%, about 32%, about 34%, or about 35% w/w of the composition.

In some embodiments, the benzopyran is a chromanol. In some embodiments, the chromanol is selected from the group consisting of: α-tocopherol, β-tocopherol, γ-tocopherol, δ-tocopherol, α-tocotrienol, β-tocotrienol, γ-tocotrienol, δ-tocotrienol, vitamin E and a combination thereof.

In some embodiments, the benzopyran is vitamin E. In some embodiments, vitamin E is present in an amount of about 1% to about 70% w/w of the composition. For example, about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 1% to about 55%, about 1% to about 60%, about 1% to about 65%, about 65% to about 70%, 6 about 0% to about 70%, about 55% to about 70%, about 50% to about 70%, about 45% to about 70%, about 40% to about 70%, about 35% to about 70%, about 30% to about 70%, about 25% to about 70%, about 20% to about 70%, about 15% to about 70%, about 10% to about 70%, or about 5% to about 70% w/w of the composition. In some embodiments, vitamin E is present in an amount of about 15% to about 35% w/w of the composition. For example, about 15% to about 17%, about 15% to about 19%, about 15% to about 21%, about 15% to about 23%, about 15% to about 25%, about 15% to about 27%, about 15% to about 29%, about 15% to about 31%, about 15% to about 33%, about 33% to about 35%, about 31% to about 35%, about 29% to about 35%, about 27% to about 35%, about 25% to about 35%, about 23% to about 35%, about 21% to about 35%, about 19% to about 35%, or about 17% to about 35% w/w of the composition. In some embodiments, the vitamin E is present in an amount of about 2%, about 15%, about 16%, about 17%, about 18%, about 19%, about 20%, about 21%, about 22%, about 23%, about 24%, about 25%, about 26%, about 27%, about 28%, about 28.15%, about 28.25%, about 28.35%, about 28.45%, about 28.55%, about 28.65%, about 28.75%, about 28.85%, about 28.95%, about 29%, about 30%, about 31%, about 32%, about 34%, or about 35% w/w of the composition.

In some of any of the above embodiments, the composition further comprises one or more excipients, diluents, or carriers.

In some embodiments, a composition as described herein is formulated for oral delivery. A composition as described herein can be formulated for oral delivery in a variety of ways. For example, the composition can be in the form of a tablet or powder. As another example, a composition as described herein can be in the form of a liquid, solution, suspension, gummy, tablet, powder, soft gelatin capsules, or hard gelatin capsules. Commercial dietary supplements are generally formulated for oral administration. For oral administration, tablets or capsules can be prepared by conventional means with pharmaceutically acceptable excipients such as binding agents, fillers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. For example, a composition as described herein can be presented as dry powder and dissolved in a suitable liquid carrier. In some embodiments, a composition as described herein can be diluted in a suitable liquid carrier. In some embodiments, a composition as described herein is diluted in an energy drink. In some embodiments, liquid preparations also can contain pharmaceutically acceptable additives such as suspending agents, emulsifying agents, non-aqueous vehicles, preservatives, buffer salts, flavoring agents, coloring agents, and sweetening agents as appropriate. In some embodiments, a composition as described herein can be presented as a stick pack. Preparations for oral administration can be suitably formulated to give controlled release of the compound.

Tablets and powders can be configured to have a unit dosage equal to the daily desired dosage. For example, if a subject desires 1000 mg of a particular composition, each tablet can be 1000 mg in weight. As another example, if a subject desires 1000 mg of a particular composition each tablet can be 500 mg in weight and the subject can take two tablets. The dosages of a particular composition will depend on many factors including the mode of administration. As an example, a composition as described herein can be formulated in a dose such that an individual receives the weight percentages as shown in Table 1, e.g., in a single tablet, divided among 2 or more tablets, or as a powder.

TABLE 1

| Components | Weight Percentage (%) |
|---|---|
| Epicatechin | 0.75% |
| Vitamin A | 4.5% |
| Vitamin C | 66% |
| Vitamin E | 28.75% |

In addition, a composition provided herein can contain a pharmaceutically acceptable carrier for in vivo administration to a subject. Such pharmaceutically acceptable carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include water, alcohol, saline, and buffered solutions. Pharmaceutically acceptable carriers also can include physiologically acceptable aqueous vehicles (e.g., physiological saline) or other known carriers appropriate to specific routes of administration. Preservatives, flavorings, and other additives such as, for example, proteins, anti-microbials, chelating agents, inert gases, and the like also can be present in a composition.

Methods

Also provided herein are methods for decreasing oxidative stress in a subject in need thereof comprising administering to the subject any of the compositions as described herein. Also provided herein are methods for decreasing oxidative stress levels in a subject in need thereof comprising administering to the subject any of the compositions as described herein.

In some embodiments, oxidative stress is associated with one or more of: cellular toxicity, infection, cancer, cardiovascular diseases such as atherosclerosis, neurodegenerative diseases such as Parkinson's disease, Alzheimer's disease, amyotrophic lateral sclerosis (ALS), multiple sclerosis, depression, and memory loss, obesity, stress, diabetes mellitus, or aging.

In some embodiments, the composition is administered orally.

EXAMPLES

Example 1. In Silico Simulations of Compositions for Reducing Oxidative Stress

Protocol

The in silico simulations were performed using CytoSolve®, a commercially available tool that enables the computational modeling of biomolecular pathways. CytoSolve® can scale and model highly complex biomolecular phenomena by its ability to integrate and couple the computations of smaller biomolecular pathways (see, e.g., Ayyadurai et al. *Cancers*. 2022, 14, 756; Ayyadurai and Deonikar, *Clin. Nutr. ESPEN*, 2021, 46, pp. 439-452; Ayyadurai and Forbes-Dewey Jr. *Cellular and Molecular Bioengineering*. 2011, 4(1):28-45; Nordsletten. *IEEE Trans Biomed Eng*. 2011; 58(12):3508-12; Ayyadurai and Deonikar. *Agricultural Sciences*. 2015; 6:630-662; Ayyadurai. *Commun Med Care Compunetics*. 2011; 1:115-168; Koo et al. *Biophys J*. 2013; 104(10):2295-306; Sweeney et al. *Nat Neurosci*. 2016; 19(6):771-83; and Ayyadurai. (2007) Scalable Computational Architecture for Integrating Biological Pathway Models (Doctoral Dissertation, Massachusetts Institute of Technology).

CytoSolve® platform was used to model mechanisms of oxidative stress in endothelial cells that included production of ROS and oxidative stress signaling. Once these pathways were integrated using CytoSolve®, the resulting biomolecular computational model was used to identify the ranges of concentrations of epicatechin, vitamin A, vitamin C, and vitamin E, which elicit a synergistic effect on the biomarker, ROS (see Table 1). Three scenarios were simulated biomolecular computational model on the CytoSolve® platform over a period of about two days: 1) Control (ROS concentrations without the supplementation of the composition described herein); 2) Effect of composition herein in Table 1 on ROS concentration over a period of seven (7) days; and, 3) Effect of composition herein in Table 1 on ROS concentration over a period of thirty (30) days. The amounts of epicatechin, vitamin A, vitamin C, and vitamin E, from Table 1 were used to model the individual as well as synergistic effect on ROS concentration versus the control over a period of seven (7) and thirty (30) days of supplementation.

Results

Figure 1:
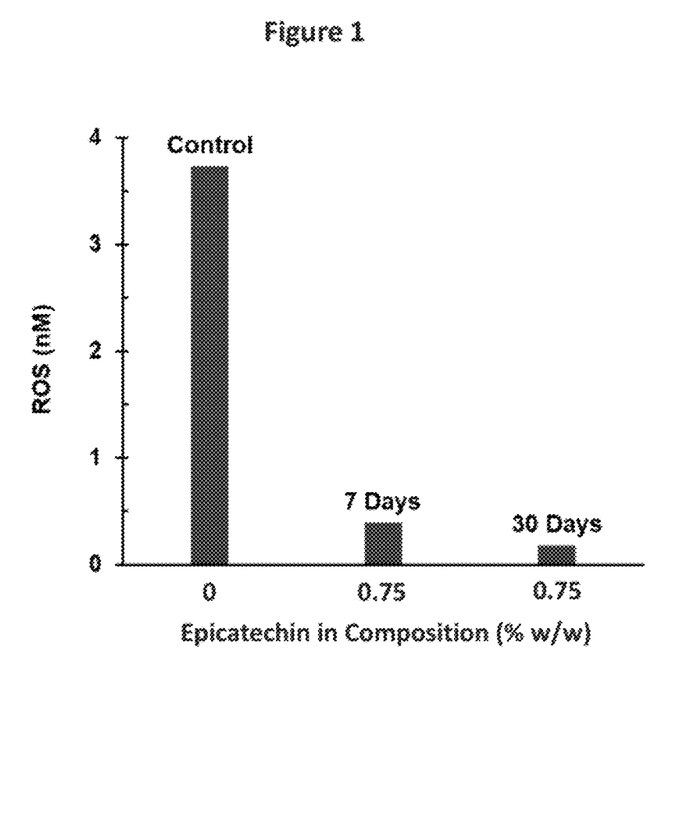
FIG. 1 is a bar graph comparing the steady state concentrations of ROS for individuals experiencing oxidative stress without supplementation of composition described herein, individuals experiencing oxidative stress with supplementation of only epicatechin in composition described herein over a period of seven (7) days and thirty (30) days. The plot is based on a biomolecular computational model using CytoSolve® and modeling mechanisms of oxidative stress. The results show that for individuals experiencing oxidative stress without supplementation of composition, the ROS levels are 3.72 nM, whereas for in individuals experiencing oxidative stress with supplementation of only epicatechin in composition, the ROS levels fall to 0.39 nM and 0.18 nM over 7-day and 30-day periods, respectively.

FIG. 1 was derived using CytoSolve® to model mechanisms of oxidative stress in endothelial cells. The results in FIG. 1 represent the steady state concentrations of ROS. Under control conditions, the concentrations of ROS were estimated to be 3.72 nM. Supplementation of only epicatechin present in the composition over a period of 7 days and 30 days led to ROS concentration of 0.39 nM and 0.18 nM respectively. These results show that epicatechin alone is able to reduce the ROS levels substantially.

Figure 2:
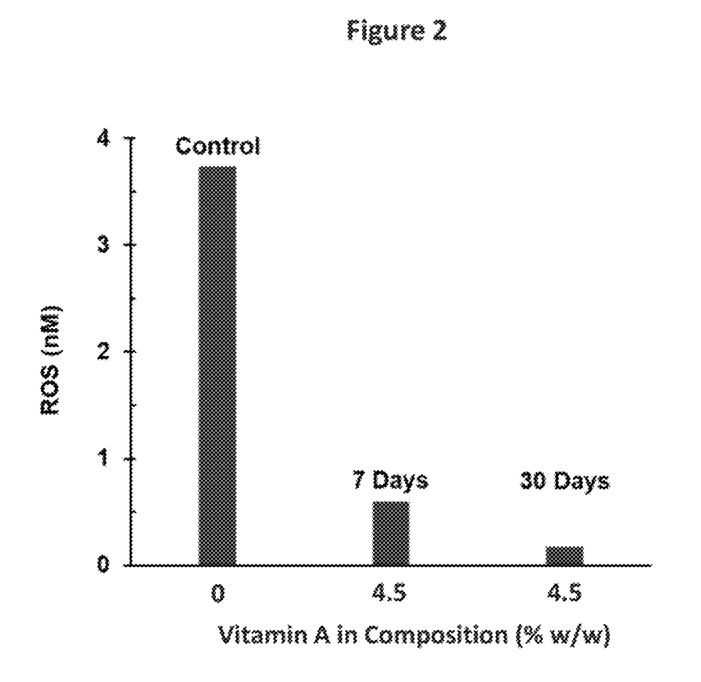
FIG. 2 is a bar graph comparing the steady state concentrations of ROS for individuals experiencing oxidative stress without supplementation of composition described herein, individuals experiencing oxidative stress with supplementation of only vitamin A in composition described herein over a period of seven (7) days and thirty (30) days. The plot is based on a biomolecular computational model using CytoSolve® and modeling mechanisms of oxidative stress. The results show that for individuals experiencing oxidative stress without supplementation of composition, the ROS levels are 3.72 nM, whereas for in individuals experiencing oxidative stress with supplementation of only vitamin A in composition, the ROS levels fall to 0.59 nM and 0.17 nM over 7-day and 30-day periods, respectively.

FIG. 2 was derived using CytoSolve® to model mechanisms of oxidative stress in endothelial cells. The results in FIG. 2 represent the steady state concentrations of ROS. Under control conditions, the concentrations of ROS were estimated to be 3.72 nM. Supplementation of only vitamin A present in the composition over a period of 7 days and 30 days led to ROS concentration of 0.59 nM and 0.17 nM respectively. These results show that vitamin A alone is able to reduce the ROS levels substantially.

Figure 3:
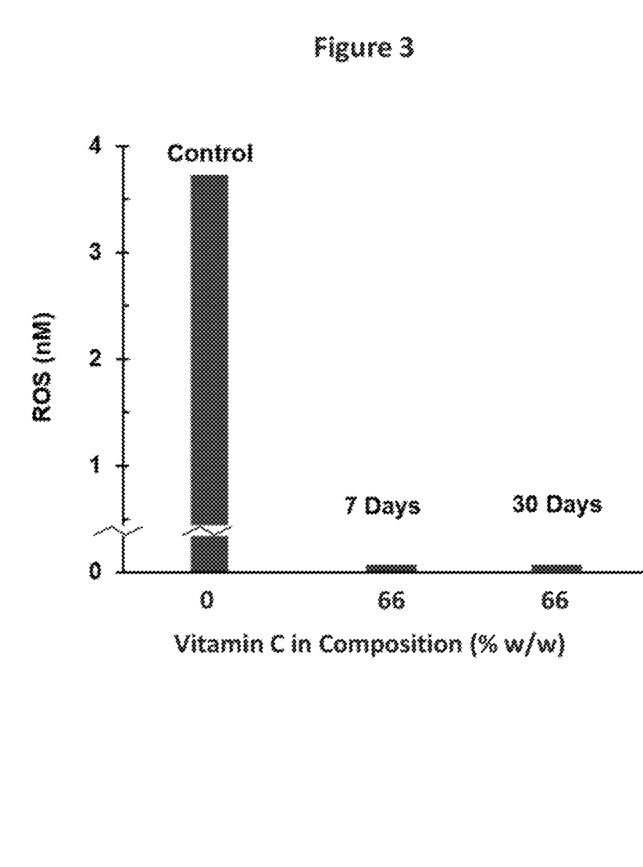
FIG. 3 is a bar graph comparing the steady state concentrations of ROS for individuals experiencing oxidative stress without supplementation of composition described herein, individuals experiencing oxidative stress with supplementation of only vitamin C in composition described herein over a period of seven (7) days and thirty (30) days. The plot is based on a biomolecular computational model using CytoSolve® and modeling mechanisms of oxidative stress. The results show that for individuals experiencing oxidative stress without supplementation of composition, the ROS levels are 3.72 nM, whereas for in individuals experiencing oxidative stress with supplementation of only vitamin C in composition, the ROS levels fall to $3.99 \times 10^4$ nM and $4.64 \times 10^{-9}$ nM over 7-day and 30-day periods, respectively.

FIG. 3 was derived using CytoSolve® to model mechanisms of oxidative stress in endothelial cells. The results in FIG. 1 represent the steady state concentrations of ROS. Under control conditions, the concentrations of ROS were estimated to be 3.72 nM. Supplementation of only vitamin C present in the composition over a period of 7 days and 30 days led to ROS concentration of $3.99 \times 10^4$ nM and $4.64 \times 10^{-9}$ nM respectively. These results show that vitamin C alone is able to reduce the ROS levels substantially.

Figure 4:
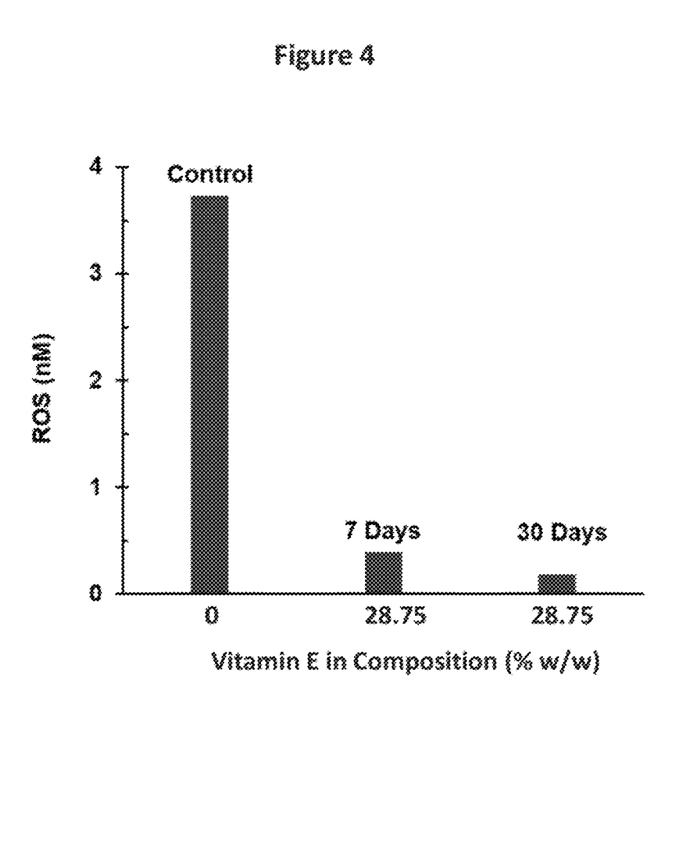
FIG. 4 is a bar graph comparing the steady state concentrations of ROS for individuals experiencing oxidative stress without supplementation of composition described herein, individuals experiencing oxidative stress with supplementation of only vitamin E in composition described herein over a period of seven (7) days and thirty (30) days. The plot is based on a biomolecular computational model using CytoSolve® and modeling mechanisms of oxidative stress. The results show that for individuals experiencing oxidative stress without supplementation of composition, the ROS levels are 3.72 nM, whereas for in individuals experiencing oxidative stress with supplementation of only vitamin E in composition, the ROS levels fall to 0.39 nM and 0.1 nM over 7-day and 30-day periods, respectively.

FIG. 4 was derived using CytoSolve® to model mechanisms of oxidative stress in endothelial cells. The results in FIG. 1 represent the steady state concentrations of ROS. Under control conditions, the concentrations of ROS were estimated to be 3.72 nM. Supplementation of only vitamin E present in the composition over a period of 7 days and 30 days led to ROS concentration of 0.39 nM and 0.10 nM respectively. These results show that vitamin E alone is able to reduce the ROS levels substantially.

Figure 5:
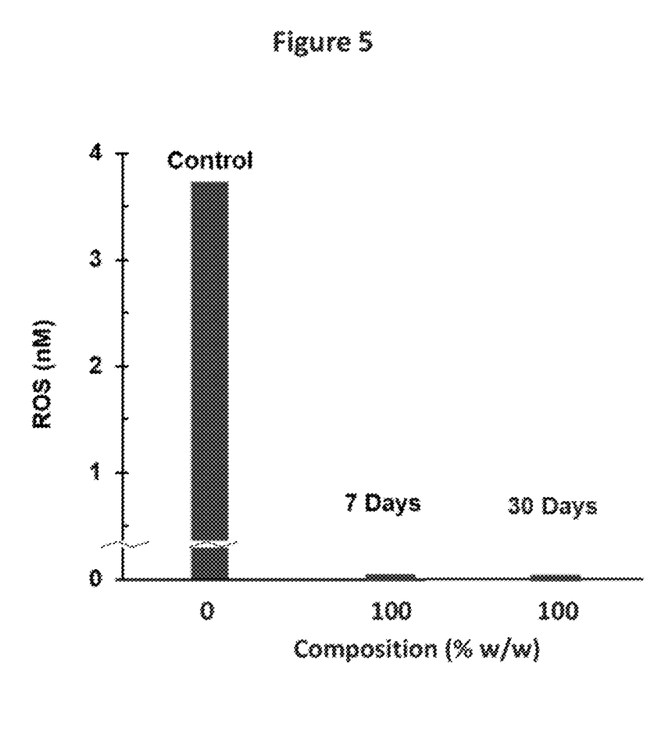
FIG. 5 is a bar graph comparing the steady state concentrations of ROS for individuals experiencing oxidative stress without supplementation of composition described herein, individuals experiencing oxidative stress with supplementation of the entire composition described herein over a period of seven (7) days and thirty (30) days. The plot is based on a biomolecular computational model using CytoSolve® and modeling mechanisms of oxidative stress. The results show that for individuals experiencing oxidative stress without supplementation of composition, the ROS levels are 3.72 nM, whereas for in individuals experiencing oxidative stress with supplementation of the entire composition, the ROS fall to $1.32 \times 10^4$ nM and $1.43 \times 10^{-12}$ nM over 7-day and 30-day periods, respectively. These results indicate that supplementation of the composition described herein lowered oxidative stress substantially.

FIG. 5 was derived using CytoSolve® to model mechanisms of oxidative stress in endothelial cells. The results in FIG. 1 represent the steady state concentrations of ROS. Under control conditions, the concentrations of ROS were estimated to be 3.72 nM. Supplementation of combination of epicatechin, vitamin A, vitamin C, and vitamin E in the composition over a period of 7 days and 30 days led to ROS concentration of $1.32 \times 10^{-4}$ nM and $1.43 \times 10^{-12}$ nM respectively. These results show that vitamin C alone is able to reduce the ROS levels substantially.

Example 2. In Vitro Efficacy Testing of Compositions for Reducing Oxidative Stress Protocol The in vitro efficacy testing of compositions for reducing ROS levels to mitigate oxidative stress are being conducted using endothelial cell culture model as described in Sabando et al., 2020 (see, e.g., Sabando et al. *Biol Res* 53: 55, which is incorporated by reference herein in its entirety). Experiments are being conducted with and without the application of the composition described herein. ROS concentrations will be measured in the cell culture as an indicator of oxidative stress. Samples from cell culture can be withdrawn and tested for ROS concentration using fluorescence spectroscopy (see, for example, Pavelescu, L. A. *J. Med. Life.* 2015, 8 (Spec Issue): 38-42; Woolley et al. *Trends Biochem. Sci.* 2013. November; 38(11):556-65.; and Yannick et al. *Oxid Med Cell Longev.* 2012 April; 2013, Article ID 862423, 15 pages; each of which are incorporated by reference herein in their entireties).

Expected Results

Comparison of ROS concentration levels in the cell culture with and without application of composition described herein will be performed to determine the efficacy of the composition in lowering oxidative stress.

Example 3. Clinical Efficacy Testing of Composition on Reducing Oxidative Stress Protocol Clinical efficacy studies are being conducted for the composition described herein using up to 100 subjects over a period of four (4) week. The clinical study protocol is described below.

Study Group Selection
1. Inclusion Criteria
   a. Gender: Male and Female
   b. Non-smoking status
   c. Age: 18-55 years
   d. BMI: 24-40 kg/m$^2$
   e. Maintenance of normal exercise and activity patterns
   f. Total cholesterol ≤7.758 mmol/L (300 mg/dl)
   g. Triglyceride concentration ≤3.387 mmol/L (300 mg/dl)
2. Exclusion Criteria:
   a. Individuals with chronic illness such as high blood pressure, diabetes
   b. Individuals receiving prescription medication
   c. Individuals taking antioxidant supplements Study Type Selection
   Placebo-controlled Randomized clinical study: Random allocation to either the group receiving the supplement under investigation or to a group receiving placebo treatment as the control Study Design Type
   Parallel-group: Each participant is randomly assigned to a group, and all the participants in the group receive (or do not receive) composition described herein.

Outcome Measurements
1. Will be based on plasma metabolites
2. Will include primary outcome and secondary outcome
3. Can be self-monitored questionnaire (or a smartphone app) or reported by people who know the individual participating in the study Results Results obtained from the clinical study will be analyzed to determine efficacy of composition described herein using the following steps:
1. Perform appropriate statistical tests to estimate the change levels in the 95% confidence interval for the two study groups where the outcome measure is in the form of ordinal level scale. Examples of such test include:
   a. Wilcoxson Rank-Sum test
   b. Mann-Whiney U test
2. Perform an intention-to-treat (ITT) analysis to overcome the issue arising from dropouts i.e. "Attrition bias."

OTHER EMBODIMENTS

It is to be understood that while the invention has been described in conjunction with the detailed description thereof, the foregoing description is intended to illustrate and not limit the scope of the invention which is defined by the scope of the appended claims. Other aspects, advantages, and modification are within the scope of the following claims.

What is claimed is:

1. A composition consisting of agents for reducing oxidative stress and optionally one or more excipients, diluents and carriers, wherein the agents consist of:
    epicatechin present in an amount of about 0.75% w/w of the composition;
    vitamin A present in an amount of about 4.5% w/w of the composition;
    vitamin C present in an amount of about 66% w/w of the composition; and,
    vitamin E present in an amount of about 28.75% w/w of the composition.

2. The composition of claim 1, wherein the composition consists of one or more excipients, diluents and carriers.

3. The composition of claim 1, wherein the composition is configured as a powder.

4. A method for reducing ROS levels of a subject comprising administering to the subject a composition of claim 1.

5. The method of claim 4, wherein the composition is administered orally.

* * * * *